United States Patent [19]

Peters

[11] Patent Number: 5,690,222
[45] Date of Patent: Nov. 25, 1997

[54] PACKAGE RETAINER FOR SURGICAL SCREW

[75] Inventor: Robert C. Peters, Clearwater, Fla.

[73] Assignee: Linvatec Corporation, Largo, Fla.

[21] Appl. No.: 701,183

[22] Filed: Aug. 21, 1996

Related U.S. Application Data

[63] Continuation of Ser. No. 418,699, Apr. 7, 1995, abandoned.

[51] Int. Cl.$^6$ ........................................ B65D 85/24
[52] U.S. Cl. ........................ 206/339; 206/364; 206/438; 206/588; 206/592
[58] Field of Search .................................. 206/339, 363, 206/438, 461, 467, 523, 591, 592, 588, 439, 368

[56] References Cited

U.S. PATENT DOCUMENTS

| | | | |
|---|---|---|---|
| Re. 33,970 | 6/1992 | Butler | 206/523 X |
| D. 273,565 | 4/1984 | Driskell et al. . | |
| 1,926,916 | 9/1933 | Reeves | 206/523 X |
| 3,301,392 | 1/1967 | Regan, Jr. . | |
| 3,696,920 | 10/1972 | Lahay . | |
| 3,910,410 | 10/1975 | Shaw | 206/363 |
| 3,983,996 | 10/1976 | Hendren, III . | |
| 4,101,031 | 7/1978 | Cromie . | |
| 4,111,302 | 9/1978 | Roth . | |
| 4,169,179 | 9/1979 | Bussey, Jr. | 206/523 |
| 4,216,860 | 8/1980 | Heimann . | |
| 4,324,331 | 4/1982 | Ignasiak . | |
| 4,453,629 | 6/1984 | Goldberg . | |
| 4,524,868 | 6/1985 | Buckley et al. . | |
| 4,576,282 | 3/1986 | Kapralis . | |
| 4,640,418 | 2/1987 | Lowry | 206/499 |
| 4,657,138 | 4/1987 | Watson . | |
| 4,730,729 | 3/1988 | Monch . | |
| 4,739,778 | 4/1988 | Christie . | |
| 4,746,614 | 5/1988 | Devaney, Jr. et al. . | |
| 4,807,752 | 2/1989 | Chodorow . | |
| 4,842,141 | 6/1989 | Segal . | |
| 4,848,541 | 7/1989 | Paliotta et al. . | |
| 5,031,775 | 7/1991 | Kane . | |
| 5,082,112 | 1/1992 | Dunklee . | |
| 5,131,537 | 7/1992 | Gonzales . | |
| 5,133,454 | 7/1992 | Hammer . | |
| 5,176,258 | 1/1993 | Antal . | |
| 5,201,825 | 4/1993 | Artusi et al. . | |
| 5,246,109 | 9/1993 | Markle et al. . | |
| 5,368,160 | 11/1994 | Leuschen et al. | 206/339 |

FOREIGN PATENT DOCUMENTS

| | | |
|---|---|---|
| 1030845 | 5/1966 | United Kingdom . |
| 1580791 | 12/1980 | United Kingdom . |

*Primary Examiner*—David T. Fidei
*Attorney, Agent, or Firm*—Gene Warzecha

[57] ABSTRACT

A flexible surgical screw retainer and method for holding a surgical screw within a sterilizable package and dispensing the screw in a controlled manner at a selected site. The retainer has an elongated recess into which a surgical screw may be placed in order to be retained by frictional engagement with the side walls of the recess. The recess is sized to any of a variety of screw sizes. When the package is opened, the surgical screw retainer may be removed and grasped by a user and squeezed in order to disengage the screw from the recess and enable it to fall to a selected surface.

10 Claims, 4 Drawing Sheets

PACKAGE RETAINER FOR SURGICAL SCREW

This is a continuation application of application Ser. No. 08/418,699, filed Apr. 7, 1995, now abandoned.

BACKGROUND OF THE INVENTION

1. Field of the Invention

This invention relates to packages for retaining surgical devices. In particular, this invention relates to a sterilizable package for retaining a surgical screw and enabling the controlled removal of the screw in a manner which does not compromise its sterility.

2. Description of the Prior Art

Surgical devices which are sold sterile are produced in sealed packages which retain the device and enable the sterilization of the device held within the package. With respect to certain surgical devices which include sharp edges, the sealed package often includes additional components for holding the surgical device in such a way as to prevent the sharp edges from either puncturing the package, thereby compromising sterility, or abrading the interior of the package thereby creating particulate matter which may make the product unsuitable for use. With respect to certain surgical devices, the internal components within the package also serve to protect the product from damage during shipment.

The foregoing considerations are quite apparent in the packaging of surgical screws. For example, surgical screws are often packaged individually in a flexible pouch which is sealable and permeable to the sterilizing agent such as gamma radiation or ethylene oxide. In certain circumstances, the pouch is replaced with a thermoformed plastic container or tray sealed along a peripheral flange with a removable lid, the lid being permeable to the sterilizing agent. Additional support for the screw may be provided by components placed into the package to prevent the screw from randomly moving about within the container interior. These package components are generally made of foam material which has the potential of producing particulate matter. Furthermore, these foam inserts are often merely pressed against a surface of the package and do not offer any controlled dispensing of the screw when the package is opened.

Since surgical screw packages are opened at or near the surgical site in the sterile field immediately prior to use, considerable care must be taken upon opening the package. Not only is there a concern that particulate matter may contaminate the area but, because the screws are relatively small, they may become easily dropped as they are removed from the sterile package.

Prior art packages retaining surgical screws do not include retainers which facilitate the controlled removal of the screw from the package. Generally, the package is opened and the screw is caused to drop on a selected surface. Even if a package may contain a retainer adapted to positively hold a surgical screw, no prior art device is known which offers the advantages of the invention or method disclosed herein.

Accordingly it is an object of this invention to provide a package for retaining a surgical screw.

It is also an object of this invention to provide a surgical screw package having a surgical screw retainer capable of retaining the screw even after the package is opened.

It is also an object of this invention to provide a surgical screw package capable of controlling the manner in which the screw is removed from the package.

It is also an object of this invention to provide a surgical screw package capable of controllably releasing the screw from the package.

It is an additional object of this invention to provide a surgical screw package having a means for enabling a user to selectively place a screw on a selected surface without touching the screw.

It is yet another object of this invention to provide a method for retaining or selectively dispensing a surgical screw.

SUMMARY OF THE INVENTION

These and other objects are accomplished by the preferred embodiment disclosed herein which is a retainer for holding an elongated surgical screw in a sterilizable package. The retainer comprises a flexible body having a top surface, a bottom surface and a pair of opposed end surfaces. The top surface is provided with an elongated screw-receiving recess in alignment between the opposed end surfaces. The recess has a predetermined width sufficient to frictionally engage any one of a variety of surgical screws.

The objects are also accomplished by the method disclosed herein which is a method of using the above-described surgical screw retainer. The method comprises the steps of providing an elongated surgical screw and the foregoing flexible retainer and placing the surgical screw in the elongated recess to form thereby a screw/retainer assembly. This screw/retainer assembly is placed in a housing which is then sealed with a removable lid. The package may then be opened prior to use and the screw/retainer assembly may be grasped by engaging the pair of opposed, user-engageable end surfaces with opposed fingers and squeezing the assembly to thereby release the surgical screw on to a selected surface.

DESCRIPTION OF THE PREFERRED EMBODIMENT

Figure 1:
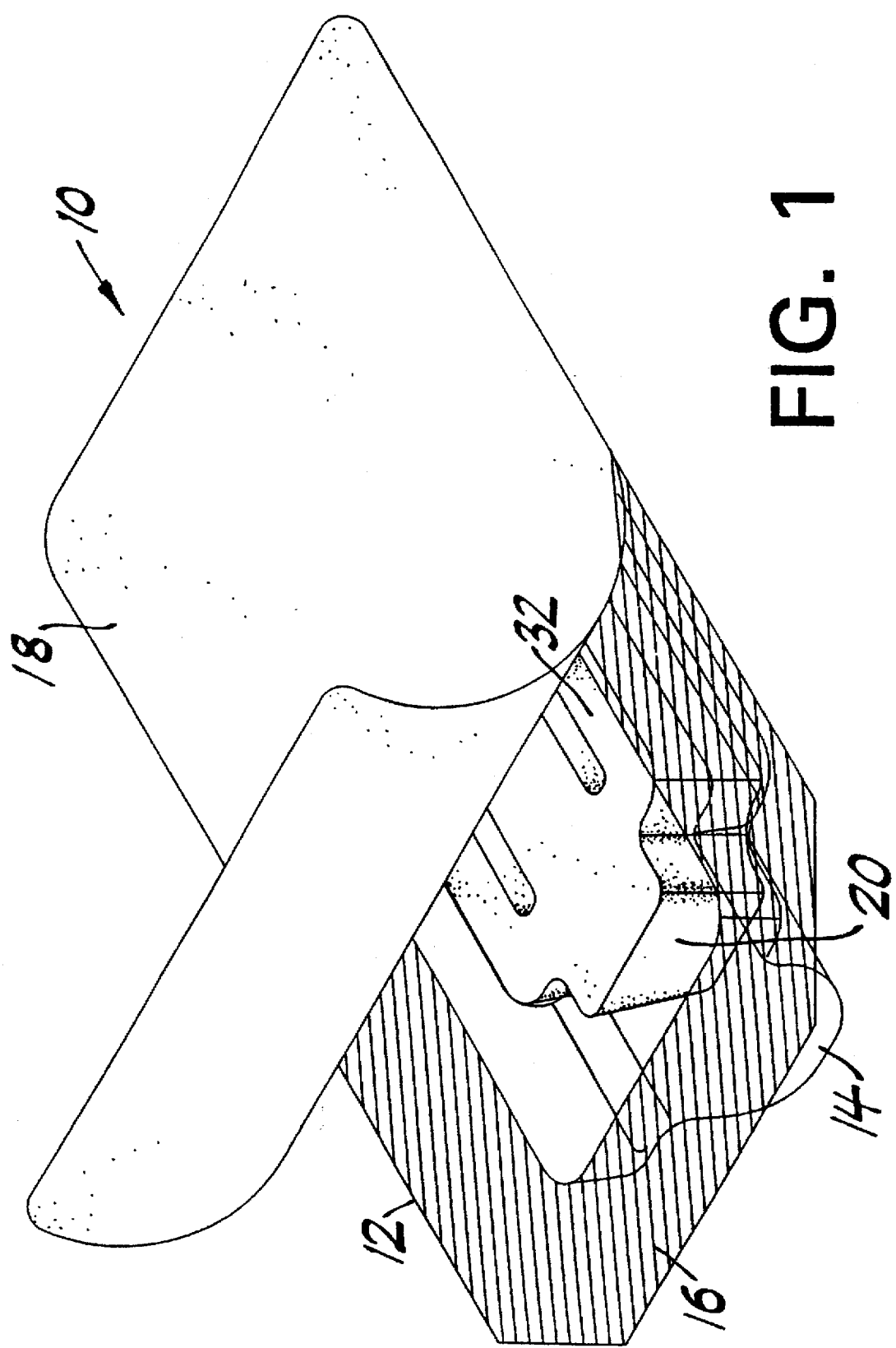
FIG. 1 is a front perspective view of a surgical screw package and retained according to the principles of this invention.

As depicted in FIG. 1, sterilizable surgical screw package 10 comprises a transparent, thermoformed container tray 12 having a body 14, peripheral flange 16 and removable lid 18. Container 12 and lid 18 are conventional packaging materials which will be well understood by those skilled in the art. For example, the tray may be formed of polyethyleneteraphthalate glycol (PETG) and the lid may be formed of a spun bonded polyolefin such as Tyvek® (a trademark of DuPont). Package 10 is designed to contain a loaded surgical screw retainer 20 (i.e. a retainer holding a screw, not shown, and sometimes referred to as a screw/retainer assembly). Body 14 and lid 18 are formed and sized in such a way as to retain the screw/retainer assembly firmly against movement within the package when it is sealed.

Figure 2:
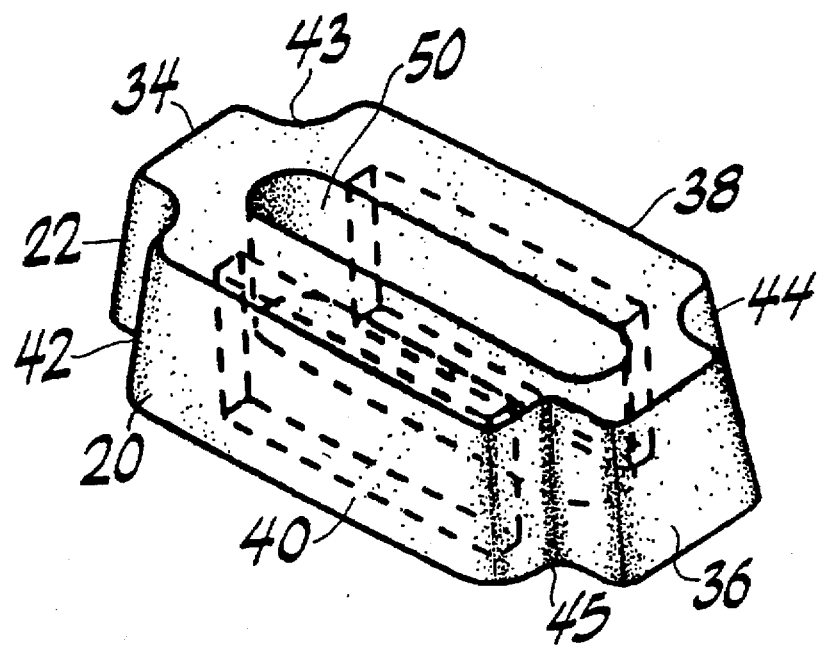
FIG. 2 shows a surgical screw retainer insert portion of FIG. 1.
Figure 3:
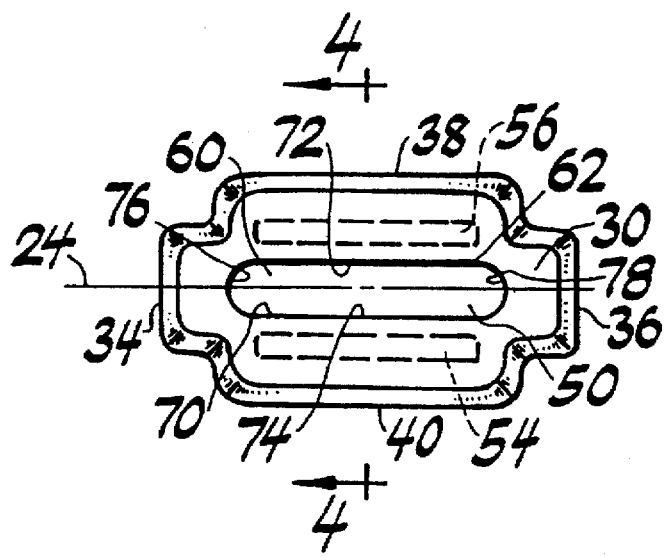
FIG. 3 is a top plan view of the surgical screw retainer of FIG. 2.
Figure 4:
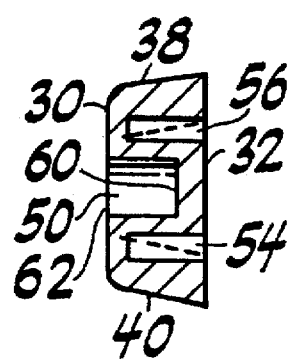
FIG. 4 is a cross-section of FIG. 3 taken along the line 4—4.

As best seen in FIGS. 2 through 4, screw retainer 20 comprises a resilient body 22 having an axis 24 and a generally rectilinear shape with top surface 30, bottom surface 32 and a peripheral surface defined by end walls 34 and 36 and side walls 38 and 40. The corners 42, 43, 44 and 45 of body 22 may be contoured as shown to minimize material usage. An elongated recess 50 is formed in top surface 30 in order to frictionally retain a surgical screw 52 (best seen in FIGS. 4 and 5) as will be better understood below. Screw 52 is known as an interference screw and does not have a head. The body of the screw has a maximum diameter at some point or points along its length and it is this diameter which provides the most frictional engagement. Recess 50 comprises a bottom or floor 60, a top or open end 62 and a peripheral side wall 70 having straight sides 72 and 74 and curved end walls 76 and 78. Bottom surface 32 is provided with a pair of axially extending recesses 54 and 56 which further enhance the flexibility of retainer 20.

The entire periphery of body 22 including side walls 38, 40 and end walls 34, 36 is tapered inwardly. Not only does this facilitate manufacture of the retainer but the incline of the end walls 34 and 36 also facilitates bending the side walls 72 and 74 of recess 50 to release the surgical screw as will be understood below. In the preferred embodiment body 22 is integrally formed in one piece from a cross-linked polyethylene foam which causes the exterior surface of retainer 20 to be relatively smooth. However, any other material may be used which can be formed into a flexible body having a surface resistant to abrasion in order to minimize any tendency to form particulate matter. A certain degree of resilience may also be helpful in order to facilitate the retention of the screw in recess 50. Preferably, the material would be thermoformable or compression moldable to produce the desired structure. The recess 50, when defined by the material of the preferred embodiment, enables peripheral wall 70 to conform to a large range of screw sizes. For example, in the preferred embodiment the dimensions of recess 50 are on the order of 1.18 inches×0.218 inches× 0.280 inches (L×W×D) and the screws may range from 7 mm×20 mm to 9 mm×30 mm. In any given configuration, retainer 20 is able to hold any one of a variety of screw sizes because of the resiliency which enables recess 50 to conform to the screw and still frictionally engage it. Thus, to accommodate a family of screws having a range of sizes, the length of recess 50 should be as long as the longest screw and the width should be as small as the narrowest screw. The depth of recess 50 should be slightly more than the radius of the largest diameter screw in the family so more than half the largest screw body will be held within recess 50.

Figure 5:
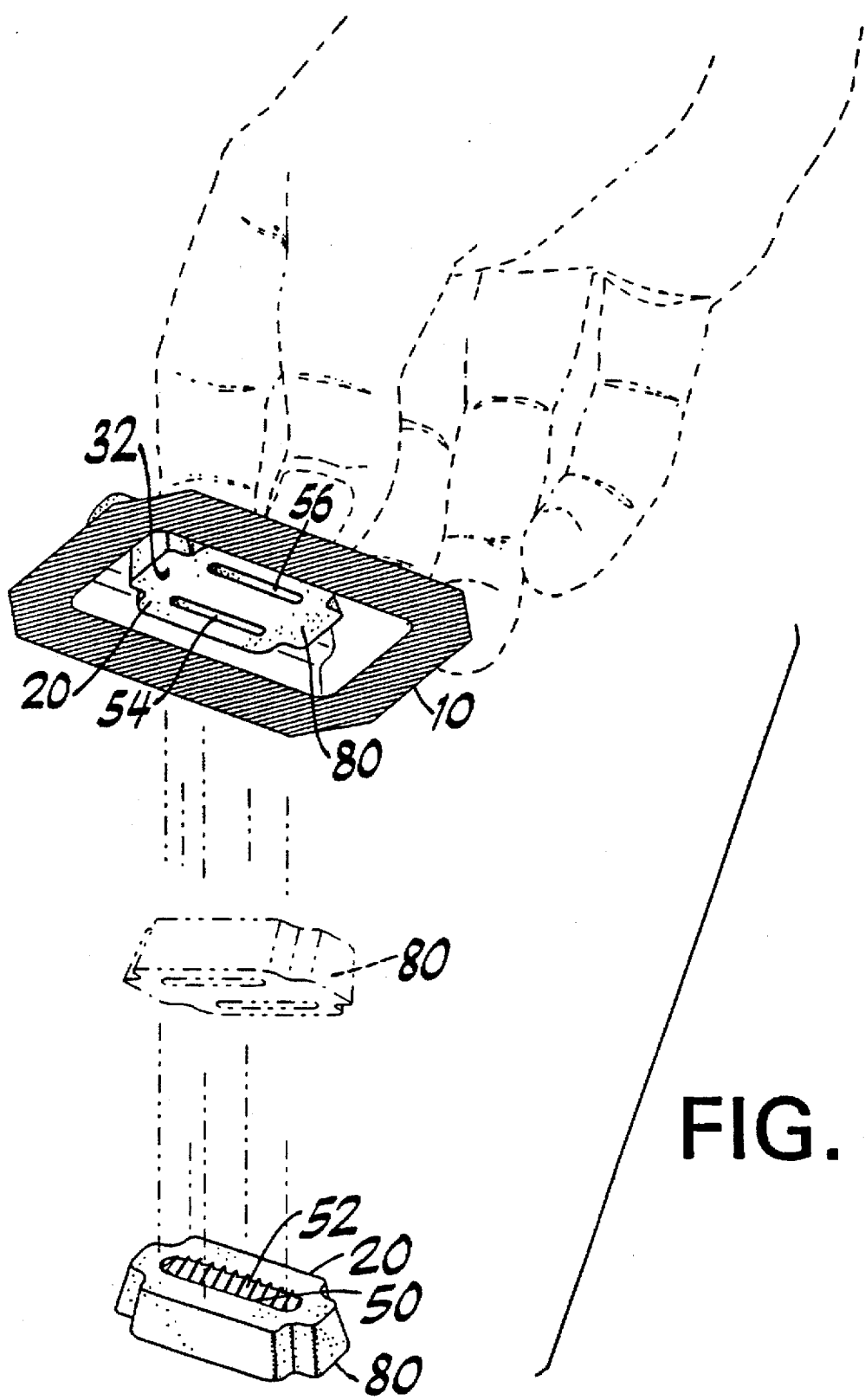
FIG. 5 is a diagrammatic representation of the method by which a surgical screw and its retainer are removed from a package.
Figure 6:
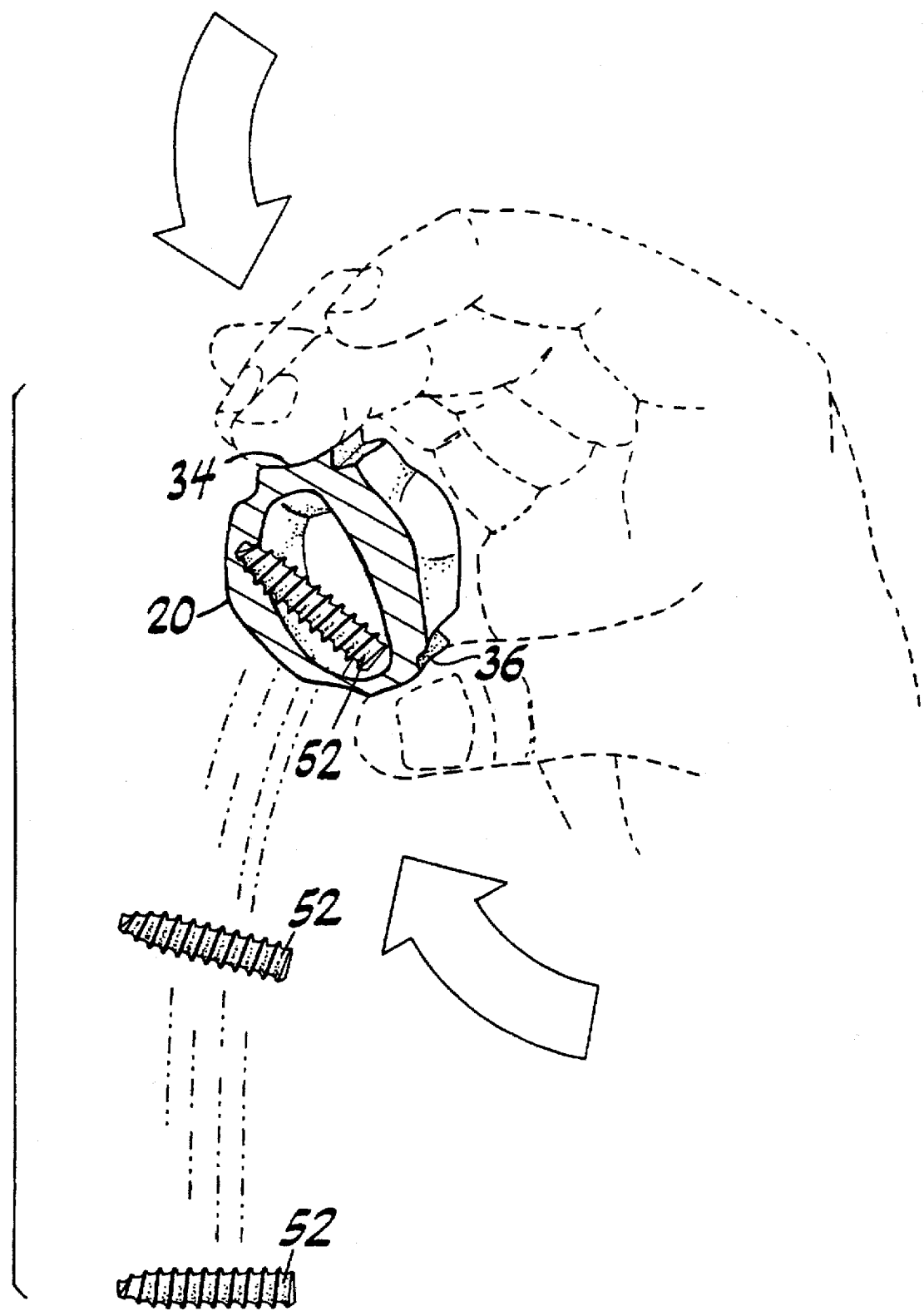
FIG. 6 is a diagrammatic representation of the method by which a surgical screw is removed from the surgical screw retainer.

The manner in which screw retainer 20 operates is best understood by reference to FIGS. 1, 5 and 6. Package 10 is first opened at the surgical site by peeling lid 18 back to allow the screw retainer with a screw to be removed from package 10. One example of how this may be done is shown in FIG. 5. Screw retainer 20 may then be grasped by a user so that ends 34 and 36 may be squeezed together along axis 24 to release screw 52. Because of the resiliency of retainer 20 and the inclined shape of end walls 34 and 36, this squeezing motion causes the end walls of recess 50 to move away from screw 52 while the floor 60 of recess 50 remains in contact with the screw. Ultimately, the screw becomes exposed out of recess 50 sufficiently to fall from retainer 20 to a selected surface. Depending upon the size of the screw retained in recess 50, the mechanics of dispensing the screw from the recess may vary. For example, in some instances the floor 60 or side walls 72, 74 may push the screw out before the ends actually release it.

The method of using the retainer 20 is best seen by reference to FIGS. 1, 5 and 6. The method comprises the steps of simply loading the screw into the recess to create a screw/retainer assembly 80, where the screw is retained by a friction fit. The assembly 80 is held within sterile package 10 until just before use. Package 10 is opened by peeling away lid 18, as shown in FIG. 1, and the assembly 80 is dropped onto a selected surface (not shown) as will be understood by reference to FIG. 5. Assembly 80 is grasped as shown in FIG. 6 to dispense the screw from the retainer.

While the invention is disclosed with respect to surgical screws, it will be understood that it is equally useful with other elongated surgical devices.

It will be understood by those skilled in the art that numerous improvements and modifications may be made to the preferred embodiment of the invention disclosed herein without departing from the spirit and scope thereof.

What is claimed is:

1. In combination, an elongated surgical screw and a retainer for holding said elongated surgical screw comprising:

a flexible body having a top surface, a bottom surface and a pair of opposed end surfaces;

an elongated screw-receiving recess formed in said top surface in alignment between said opposed end surfaces, said recess having a predetermined width sufficient to frictionally engage said surgical screw;

means for enabling said recess to be manually deformed by squeezing said opposed ends together to thereby automatically decrease the frictional engagement of said screw and eject said screw from said recess.

2. A combination according to claim 1 wherein said elongated surgical screw has an axis and a maximum predetermined diameter and wherein said elongated screw-receiving recess has a floor at a predetermined depth sufficient to enable said recess to receive and hold said surgical screw therein such that the distance between said top surface and said floor is greater than or equal to one-half said predetermined diameter.

3. A combination according to claim 1 wherein said elongated screw-receiving recess has an axis, which is transverse to said opposed end surfaces.

4. A combination according to claim 1 wherein said means for enabling comprises inclined opposed end surfaces, inclined symmetrically relative to the axis of said elongated screw receiving means.

5. A package comprising:

an elongated surgical screw;

a flexible retainer block having a top surface, a bottom surface and a pair of opposed, symmetrically tapered end surfaces;

an elongated screw-receiving recess formed in said top surface in alignment between said opposed end surfaces, said recess containing said surgical screw and having a predetermined width sufficient to frictionally engage said surgical screw;

a sterilizable housing containing said surgical screw and said flexible retainer block.

6. A system of packaging surgical screws of varying diameters and lengths comprising:

a surgical screw having a length and width;

a resilient retainer for holding said surgical screw, said retainer comprising a top surface, a bottom surface and a pair of opposed, symmetrically tapered end surfaces, an elongated screw-receiving recess formed in said top surface in alignment between said opposed end surfaces, said recess for containing said surgical screw and having a predetermined size sufficient to frictionally engage said surgical screw;

a container for holding said resilient retainer;

a cover means for closing said container.

7. A method of packaging a surgical screw comprising the steps of:

providing an elongated surgical screw;

providing a flexible retainer having a top surface, a bottom surface and a pair of opposed, symmetrically tapered end surfaces, an elongated screw-receiving recess formed in said top surface in alignment between said opposed end surfaces, said recess for containing said surgical screw and having a predetermined width sufficient to frictionally engage said surgical screw;

placing said surgical screw in said recess to form thereby a screw/retainer assembly;

placing said screw/retainer assembly in a housing;

sealing said housing with a removable lid.

8. A method according to claim 7 wherein said step of placing said screw/retainer assembly in a housing further comprises placing said recess facing away from said lid.

9. A method of removing an elongated surgical screw having an axis from a package containing the screw comprising the steps of:

providing a package comprising a sealed housing containing an assembly of a flexible retainer and a surgical screw frictionally retained within said flexible retainer, said flexible retainer having a pair of opposed, user-engageable, symmetrically tapered end surfaces situated transversely to the axis of said surgical screw, said housing being sealed with a removable lid;

opening the package by removing said lid to provide access to said assembly;

grasping said assembly by engaging said pair of opposed, user-engageable end surfaces with opposed fingers;

squeezing said user-engageable end surfaces together to thereby, automatically release said surgical screw.

10. A method of using a surgical object retainer comprising the steps of:

providing an elongated surgical object;

providing a flexible retainer having a top surface, a bottom surface and a pair of opposed, symmetrically tapered end surfaces, an elongated object-receiving recess formed in said top surface in alignment between said opposed end surfaces, said recess for containing said surgical object and having a predetermined width sufficient to frictionally engage said surgical object;

placing said surgical object in said recess to form thereby an object/retainer assembly;

placing said object/retainer assembly in a housing;

sealing said housing with a removable lid;

removing said removable lid;

grasping said assembly by engaging said pair of opposed, user-engageable end surfaces with opposed fingers;

squeezing said user-engageable end surfaces together to thereby, automatically release said surgical object.

* * * * *